United States Patent [19]

Buschmann et al.

[11] Patent Number: 4,602,930
[45] Date of Patent: Jul. 29, 1986

[54] PHENYLPROPYLAMMONIUM SALTS, AS GROWTH REGULANTS

[75] Inventors: Ernst Buschmann; Bernd Zeeh, both of Ludwigshafen; Johann Jung, Limburgerhof; Hubert Sauter, Mannheim, all of Fed. Rep. of Germany

[73] Assignee: BASF Aktiengesellschaft, Fed. Rep. of Germany

[21] Appl. No.: 727,131

[22] Filed: Apr. 25, 1985

Related U.S. Application Data

[62] Division of Ser. No. 213,789, Dec. 8, 1980, Pat. No. 4,554,006.

[30] Foreign Application Priority Data

Dec. 24, 1979 [DE] Fed. Rep. of Germany ....... 2952382

[51] Int. Cl.⁴ .................... A01N 33/04; C07D 207/08
[52] U.S. Cl. .......................................... 71/76; 71/74; 71/77; 71/78; 71/88; 71/94; 71/95; 260/239 B; 548/574; 548/578
[58] Field of Search .................. 71/76, 77, 78, 95

[56] References Cited

U.S. PATENT DOCUMENTS

| | | | |
|---|---|---|---|
| 3,850,611 | 11/1974 | Nakanishui et al. | 71/94 |
| 3,988,373 | 10/1976 | Nakanishi et al. | 260/514.1 |
| 4,014,678 | 3/1977 | Huppi et al. | 71/94 |
| 4,139,367 | 2/1979 | Huppi et al. | 71/94 |
| 4,202,894 | 5/1980 | Pfiftner | 514/227 |
| 4,554,006 | 11/1985 | Buschmann et al. | 71/76 |

FOREIGN PATENT DOCUMENTS 1310372 3/1973 United Kingdom .

OTHER PUBLICATIONS

N. Tolbert, (2-Chloroethyl)trimethylammonium Chloride as Growth Regulant; *J. Biol. Chem.* vol. 235, No. 7, pp. 495–499 (1960).

*Primary Examiner*—Donald G. Daus
*Assistant Examiner*—G. Hendricks
*Attorney, Agent, or Firm*—Keil & Weinkauf

[57] ABSTRACT

Phenylpropylammonium salts of the formula

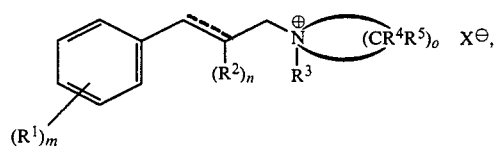

where $R^1$ denotes for instance alkyl or halogen, $R^2$ denotes for instance alkyl or alkoxy, $R^3$ denotes alkyl, alkenyl or alkynyl of up to 6 carbon atoms, $R^4$ and $R^5$ denote hydrogen or alkyl of up to 3 carbon atoms, m denotes one of the integers 0, 1, 2 and 3, n denotes one of the integers 0, 1 and 2, o denotes one of the integers 4, 5 and 6, $X^\ominus$ denotes an anion, and the dashed bond may be hydrogenated when n is 0 or 1, and is hydrogenated when n is 2; the preparation of these compounds; and agents for regulating plant growth containing these compounds as active ingredients.

3 Claims, No Drawings

PHENYLPROPYLAMMONIUM SALTS, AS GROWTH REGULANTS

This is a division of application Ser. No. 213,789, filed Dec. 8, 1980, now U.S. Pat. No. 4,554,066.

The present invention relates to novel, quaternary phenylpropylammonium salts, processes for their manufacture, and agents containing these compounds which are suitable for regulating plant growth.

The growth-regulating properties of 2-chloroethyl-trimethylammonium chloride (CCC) (J. Biol. Chem., 235, 475, 1960) in cereals and other crops have been disclosed (U.S. Pat. No. 3,156,554). Other ammonium salts having a growth-regulating action have also been disclosed (German Laid-Open Application DE-OS Nos. 2,017,497; 2,114,512; and 2,459,129).

When these prior art agents are used for regulating plant growth, their action, particularly at low application rates and concentrations, is often insufficient.

We have now found novel phenylpropylammonium salts of the formula

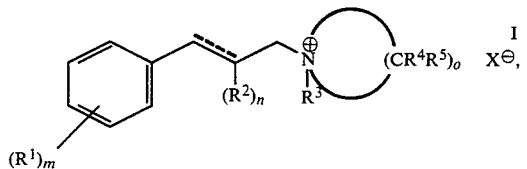

where $R^1$ denotes alkyl, cycloalkyl, alkoxy, acyl or halogen, $R^2$ denotes alkyl, alkenyl or alkoxy, $R^3$ denotes $C_1$-$C_6$-alkyl, $C_3$-$C_6$-alkenyl or alkynyl, $R^4$ and $R^5$ denote hydrogen or $C_1$-$C_3$-alkyl, m denotes one of the integers 0, 1, 2 and 3, n denotes one of the integers 0, 1 and 2, o denotes one of the integers 4, 5 and 6, $X^\ominus$ denotes the anion of a non-phytotoxic acid, and the dashed bond may be hydrogenated when n is 0 or 1, and is hydrogenated when n is 2. The term "propyl", for the purposes of the invention, thus also embraces monounsaturated propyl, viz., propenyl. Agents containing these new compounds as active ingredients have powerful growth-regulating properties.

Examples of meanings for $R^1$ are 2-methyl, 3-methyl, 4-methyl, 4-tert-butyl, 3-methyl-4-chloro, 2-methyl-4-chloro, 4-cyclopentyl, 4-cyclohexyl, 4-methoxy, 4-acetyl, 4-propionyl, 2-chloro, 4-chloro, 2,4-$Cl_2$, 2,3,4-$Cl_3$, 2,4,5-$Cl_3$,4-bromo and 2-fluoro.

Examples of meanings for $R^2$ are methyl, ethyl, n-propyl, isopropyl, n-butyl, isobutyl, n-pentyl, prop-1-enyl, but-1-enyl, methoxy and ethoxy.

Examples of meanings for $R^3$ are methyl, ethyl, propyl, n-butyl, isobutyl, allyl, crotyl, propynyl and butynyl.

Examples of meanings for $R^4$ and $R^5$ are hydrogen, methyl, ethyl, n-propyl and isopropyl. Taking into account that o is 4, 5, or 6, the radical —N(CR$^4$R$^5$)$_o$ is, in the simplest cases (i.e., when $R^4$ and $R^5$ are hydrogen), pyrrolidine, piperidine or hexamethylenimine. These are preferred because of their ease of accessibility. When these heterocycles are substituted ($R^4$ and/or $R^5$=$C_1$-$C_3$-alkyl), those are preferred in which from 1 to 3 of the methylene radicals are substituted and bear in each case only one substituent. When the methylene radicals are disubstituted, methyl and ethyl are preferred.

The upper carbon limit for $R^1$ and $R^2$ is not restricted to 5; radicals having from 1 to 4 carbon atoms are preferred, but radicals with 6 carbon atoms are also suitable.

By "non-phytotoxic anions", we mean those which, at the rates the active ingredient is applied, do not impair its effectiveness and thus present no phytotoxic hazards. Particularly suitable examples of such anions are iodine, bromine, chlorine, sulfate, tosylate, mesylate, dodecylsulfonate, dodecylphenylsulfonate and 4-bromophenylsulfonate, as these are usually obtained on manufacture of the compounds. They may then be replaced in conventional manner, e.g., by the anions nitrate, phosphate, acetate or benzoate. Accordingly, the anions may be mono- or polyvalent, and organic or inorganic.

The compounds according to the invention may be employed as active ingredients in growth regulators. The agents according to the invention surprisingly have a much stronger growth-regulating action on crop plants than the prior art 2-chloroethyl-trimethylammonium chloride, which is accepted as being a good compound having the same kind of action.

The starting compounds for the manufacture of the novel phenylpropylammonium salts of the formula I are phenylpropylamines (some of which are disclosed in German Laid-Open Application DE-OS No. 2,752,096) of the formula

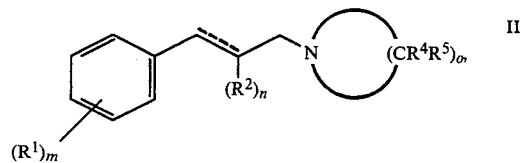

where $R^1$, $R^2$, $R^4$, $R^5$, m, n and o have the above meanings. These tertiary amines may be reacted in conventional manner with quaternizing agents to give the end compounds. Suitable quaternizing agents in addition to the alkyl, alkenyl and alkynyl ($R^3$) halides are, for example, dimethylsulfate, diethylsulfate and sulfonic acid esters of the formula R—$SO_3R^3$, R denoting $C_{1-20}$-alkyl or halogen- or alkyl-substituted phenyl.

Alternative starting materials are phenylpropyl halides of the formula

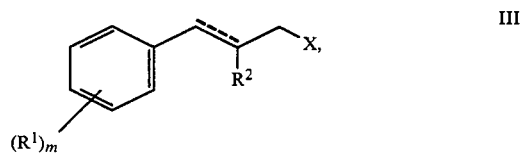

where $R^1$, $R^2$ and m have the above meanings and X denotes Cl, Br or I, some of which are also disclosed in German Laid-Open Application DE-OS No. 2,752,096.

The following scheme shows how compounds II and III may be manufactured by generally known reactions. The manufacture of the aldehydes IV is disclosed by B. Zeeh and E. Buschmann in Liebigs Ann. Chem., p. 1585, 1979.

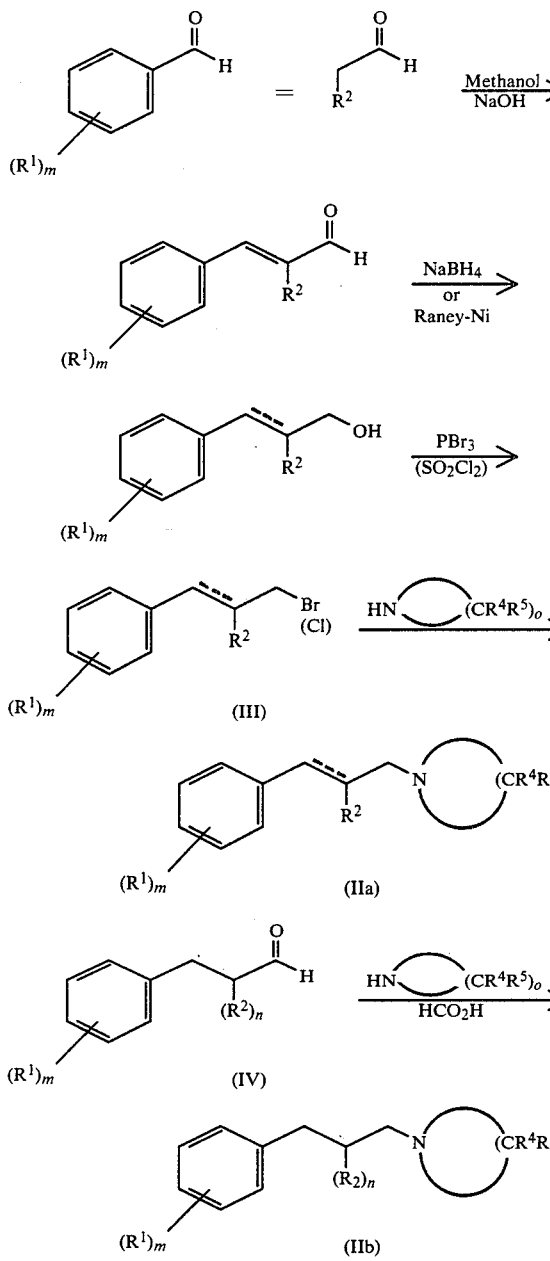

It will be clear from this scheme that the novel phenylpropylammonium salts are obtained by reacting a phenylpropylamine of the formula II with an alkylating agent of the formula $R^3X$, $R^3$ and X having the above meanings. Alternatively, the active ingredients according to the invention are obtained by reacting a phenylpropyl halide of the formula III with tertiary amines of the formula $$R^3-N\underset{}{\underbrace{(CR^4R^5)_o}} \quad V$$

where $R^3$, $R^4$, $R^5$ and o have the above meanings.

The reaction of the phenylpropylamines II with $R^3X$ and the reaction of the phenylpropyl halides III with the tertiary amines V are carried out for instance at from 10° to 150° C. in the presence or absence of a solvent, e.g., ethanol, methanol, $CHCl_3$, $CH_2Cl_2$, acetonitrile, dimethylformamide or ethyl acetate, and at atmospheric or superatmospheric pressure.

The following examples illustrate the preparation of the compounds according to the invention.

N-Crotonyl-N-[3-(2,4-dichlorophenyl)-2-methyl-2-prop-1-en-1yl-propyl]-pyrrolidinium bromide (Example 20)

A solution of 31.2 g of N-[3-(2,4-dichlorophenyl)-2-methyl-2-prop-1-en-1-yl-propyl]-pyrrolidine and 27 g of crotyl bromide in 250 ml of ethyl acetate is refluxed for 5 hours. The mixture is then stirred for 15 hours at room temperature and the crystalline product which is obtained is filtered off, washed with ether and dried in vacuo. 15 g of the desired product is obtained; m.p.: 128° C.

N-(3-(2,4-Dichlorophenyl)-2-methyl-propyl)-N-methyl-hexamethylene immonium bromide (Example 29)

19 g of methyl bromide is gassed into 300 ml of acetonitrile. After the addition of 30 g of N-[3-(2,4-dichlorophenyl)-2-methylpropyl]-hexamethylenimine, the mixture is stirred at room temperature for 15 hours and then concentrated. The residue crystallizes upon trituration with ethyl acetate. The crude product is filtered off, washed with ethyl acetate and dried in vacuo. There is obtained 18 g of N-[3-(2,4-dichlorophenyl)-2-methyl-propyl]-N-methyl-hexamethylene immonium bromide; m.p.: 178° C.

N-Allyl-N-[2-methyl-3-(o-methyl-phenyl)-propyl]-pyrrolidinium bromide (Example 24)

A solution of 51 g of N-[2-methyl-3-(o-methyl-phenyl)-propyl]-pyrrolidine and 58 g of allyl bromide in 200 ml of ethyl acetate is refluxed for 5 hours. The product precipitates as a resin. After the ethyl acetate has been decanted, the crude product is triturated several times with ethyl acetate. Supernatant solvent is decanted. Finally, the product is triturated with n-pentane and the solvent decanted. The oil which remains is freed from solvent residues in a rotary evaporator. There remains 60 g of N-allyl-N-[2-methyl-3-(o-methyl-phenyl)-propyl]-pyrrolidinium bromide as a brown resin.

The following compounds are obtainable in the same way:

TABLE 1

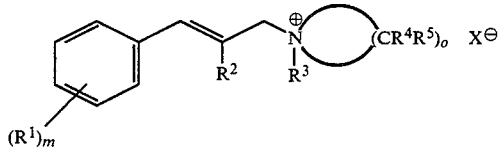

| Example No. | $(R^1)_m$ | $R^2$ | $R^3$ | $(CR^4R^5)_o$ | X | m.p. |
| --- | --- | --- | --- | --- | --- | --- |

TABLE 1-continued

| | | | | | | |
|---|---|---|---|---|---|---|
| 1 | 4-Cl | $CH_3$ | Allyl | $(CH_2)_4$ | Br | |
| 2 | 2,4-Cl | $CH_3$ | Allyl | $(CH_2)_4$ | Br | 110° |
| 3 | 2,4-Cl | $C_2H_5$ | Allyl | $(CH_2)_4$ | Br | |
| 4 | 2,4-Cl | $n-C_4H_9$ | Allyl | $(CH_2)_4$ | Br | |
| 5 | 2,4-Cl | $n-C_5H_{11}$ | Allyl | $(CH_2)_4$ | Br | 109° |
| 6 | H | H | Allyl | $(CH_2)_4$ | Br | |
| 7 | H | $CH_3$ | Allyl | $(CH_2)_4$ | Br | |
| 8 | 2,4-Cl | Isopropyl | Allyl | $(CH_2)_4$ | Br | 75° |
| 9 | 2,3,4-Cl | $n-C_4H_9$ | Allyl | $(CH_2)_4$ | Br | |
| 10 | 2,4-Cl | $OCH_3$ | Allyl | $(CH_2)_4$ | Br | |
| 10 A | 2,4-Cl | $n-C_5H_{11}$ | Allyl | $(CH_2)_5$ | Br | 148° |

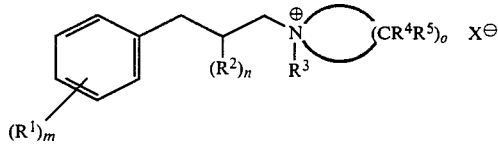

| Example No. | $(R^1)_m$ | $(R^2)_n$ | $R^3$ | $(CR^4R^5)_o$ | X | m.p. |
|---|---|---|---|---|---|---|
| 11 | 2-F | $CH_3$ | Allyl | $(CH_2)_4$ | Br | resin |
| 12 | 4-Acetyl | $CH_3$ | Allyl | $(CH_2)_4$ | Br | resin |
| 13 | 2,4-Cl | $CH_3$ | Allyl | $(CH_2)_4$ | Br | resin |
| 14 | 2,4-Cl | $CH_3$ | Allyl | $(CH_2)_4$ | Cl | |
| 15 | 4-Br | H | Allyl | $(CH_2)_4$ | Br | 127–8° |
| 16 | 4-$OCH_3$ | $CH_3$ | Allyl | $(CH_2)_4$ | Br | resin |
| 17 | 2,4,5-Cl | H | Allyl | $(CH_2)_4$ | Br | 112–115° |
| 18 | 2,4-Cl | iso-Propyl | Allyl | $(CH_2)_4$ | Br | 123° |
| 19 | 2,4-Cl | n-Propyl | Allyl | $(CH_2)_4$ | Br | resin |
| 20 | 2,4-Cl | Methyl Propen-1-yl | Crotyl | $(CH_2)_4$ | Br | 128° |
| 21 | 3-$CH_3$,4-Cl | $CH_3$ | Allyl | $(CH_2)_4$ | Br | resin |
| 22 | 4-Cl | $CH_3$ Propen-1-yl | Allyl | $(CH_2)_4$ | Br | 147° |
| 23 | 2,4-Cl | $(CH_3)_2$ | Allyl | $(CH_2)_4$ | Br | 136–8° |
| 24 | 2-$CH_3$ | $CH_3$ | Allyl | $(CH_2)_4$ | Br | resin |
| 25 | 3-$CH_3$ | $CH_3$ | Allyl | $(CH_2)_4$ | Br | |

| Example No. | $(R^1)_n$ | $(R^2)_n$ | $R^3$ | $(CR^4R^5)_o$ | X | M.p. |
|---|---|---|---|---|---|---|
| 26 | 2-Cl | $CH_3$ | Allyl | $(CH_2)_4$ | Br | 105° |
| 27 | 2,4-Cl | Methyl Propen-1-yl | Allyl | $(CH_2)_4$ | Br | 172–4° |
| 28 | 2,4-Cl | $CH_3$ | Ethyl | $(CH_2)_6$ | Br | 176–8° |
| 29 | 2,4-Cl | $CH_3$ | Methyl | $(CH_2)_6$ | Br | 178° |
| 30 | 2,4-Cl | $CH_3$ | Allyl | $(CH_2)_6$ | Br | 177–180° |
| 31 | 4-Cl | $CH_3$ | Allyl | $(CH_2)_6$ | Br | 76–77° |
| 32 | 4-Cl | $CH_3$ | Allyl | $(CH_2)_5$ | Br | 55–58° |
| 33 | 4-t-Butyl | $CH_3$ | Allyl | $(CH_2)_4$ | Br | 125° |
| 34 | 2,4-Cl | $CH_3$ | $CH_3$ | $(CH_2)_4$ | Br | resin |
| 35 | H | $CH_3$ | Allyl | $(CH_2)_4$ | Br | resin |
| 36 | 4-Cl | $CH_3$ | Allyl | $(CH_2)_4$ | Br | resin |
| 37 | 2,3,4-Cl | $CH_3$ | Allyl | $(CH_2)_4$ | Br | |
| 38 | 2,3,4-Cl | $n-C_4H_9$ | Allyl | $(CH_2)_4$ | Br | resin |
| 39 | 2,3,4-Cl | Isopropyl | Allyl | $(CH_2)_4$ | Br | |
| 40 | 2,4,5-Cl | H | Crotyl | $(CH_2)_4$ | Br | resin |
| 41 | 2,4-Cl | $CH_3$ | Crotyl | $(CH_2)_4$ | Br | resin |
| 42 | 2,4-Cl | n-Propyl | Allyl | $(CH_2)_4$ | I | |
| 43 | 2,4-Cl | $OCH_3$ | Allyl | $(CH_2)_4$ | Br | resin |
| 44 | 2,4-Cl | $CH_3$ | Allyl | $(CH_2)_3-CHCH_3CH_2$ | Br | |
| 45 | 2,4-Cl | $n-C_3H_7$ | Propynyl | $(CH_2)_4$ | Br | |
| 46 | 4-Br | $CH_3$ | Allyl | $(CH_2)_4$ | Br | resin |
| 47 | 4-$CH_3$ | $CH_3$ | Allyl | $(CH_2)_4$ | Br | resin |
| 48 | 2,4-Cl | $n-C_3H_7$ | Allyl | $(CH_2)_5$ | Br | resin |

Plant growth regulators may have several different effects on plants. The action of the compounds depends essentially on the time applied, with reference to the development stage of the seed or plant, on the amount of active ingredient applied to the plants of their habitat, and on the application method employed. At all events, growth regulators are intended to influence crop plants in a desired manner.

Plant growth-regulating compounds may be used for instance to inhibit vegetative plant growth. Such a reduction in growth is of economic interest inter alia in grass, because as a result of depressed grass growth it is possible for instance to reduce the frequency of mowing in ornamental gardens, parks, sportsgrounds and on roadsides. It is important to inhibit the growth of herbaceous and woody plants on roadsides and in the vicinity of overhead transmission lines, or quite generally where vigorous growth is undesired.

A further important application area for growth regulators is the inhibition of upward plant growth in cereals (which include rice). A reduction in stem length reduces or completely eliminates the danger of lodging before the plants are harvested. Growth regulators may also strengthen the stem of cereals, which also counteracts lodging.

The inhibition of vegetative growth also makes closer planting possible in numerous crops, which means an increase in yield based on the area cropped.

A further mechanism for increasing yields with plant growth regulators is based on the fact that blossom and fruit formation benefits to a greater extent from the nutrients when vegetative growth is restricted.

However, plant growth regulators may also frequently be employed to promote vegetative growth. This is of great use when the vegetative plant parts are harvested. The promotion of vegetative growth may, however, simultaneously result in an increase in generative growth, e.g., the formation of more or bigger fruit.

Increases in yield may also be achieved in many instances by influencing plant metabolism without there being any noticeable change in vegetative growth. Growth regulators may also change the composition of plants and thus improve the quality of the harvested products. It is for example possible to increase the sugar content of sugar beets, sugarcane, pineapples and citruses, or to raise the protein content in soybeans and cereals.

Parthenocarpic fruits may also be formed under the influence of growth regulators. Further, the sex of the flowers may be influenced.

The production or the flow of secondary plant materials may also be positively influenced with growth regulators. The stimulation of latex flow in rubber trees may be mentioned by way of example.

During the growth of the plant, branching may be increased by growth regulators as a result of the chemical control of apical dominance. This is of interest for instance in the propagation of plant cuttings. It is, however, also possible to inhibit the growth of lateral branches, e.g., to prevent sucker growth in tobacco plants after topping, and thus to promote leaf growth.

Growth regulators may also be used to defoliate plants at any desired time. Such a defoliation facilitates mechanical harvesting, e.g., in grapes or cotton, or reduces transpiration at a time when the plant is to be transplanted.

Premature fruit drop may also be prevented by growth regulators. It is, however, also possible to thin out chemically by promoting fruit drop to a certain extent. Growth regulators may also be used to reduce the force to be exerted for plucking off fruit from crop plants at harvest time, making mechanical harvesting possible, or facilitating manual harvesting.

Further, growth regulators may be used to accelerate or delay the ripening of material before or after harvesting. This feature is of particular advantage, because market needs can be optimally accommodated. Growth regulators may also in many cases improve fruit color. It is also possible to concentrate ripening with growth regulators, thus making it possible, for example in tobacco, tomatoes or coffee, to harvest completely mechanically or manually in just one operation.

Growth regulators can also influence the dormancy of seeds or bids, i.e., the annual endogenous rhythm; plants such as pineapples or ornamentals in nurseries can thus be made to germinate, sprout or blossom at a time at which they normally show no willingness to do so.

Growth regulators may further be employed to delay budding or seed germination, for example in order in frost-endangered areas to prevent damage by late frosts.

Growth regulators may also make crop plants halophilic, i.e., they may be cultivated in salty soils.

Growth regulators can also make plants more frost- and drought-resistant.

In view of the different crops in which growth regulators can be used, the various action targets, and differing soil and weather conditions, it will be clear that it is not possible to state the requisite application rates for every individual case. However, the skilled worker will have no difficulty in ascertaining the most suitable application rates because the largest useful amount is generally 5 kg of active ingredient per hectare. In soybeans, for instance, approx. 0.25 to approx. 2.5 kg/ha may be applied postemergence.

The agents are applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

As the active ingredients according to the invention are salts, aqueous formulations are preferred. They may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The agents according to the invention may additionally contain other active ingredients, e.g., herbicides and/or fungicides.

The results of biological tests with the agents according to the invention evidence a most remarkable growth-regulating action, as the figures given in the tables below show. To determine the growth-regulating properties of the active ingredients, soil provided with sufficient nutrients was filled into plastic pots about 12.5 cm in diameter and test plants were grown therein. The compounds to be tested were sprayed as a postemergence treatment onto the plants as aqueous formulations. The growth-regulating action observed was confirmed at the end of the experiment by height measurements. The values obtained were compared with those for untreated plants. The prior art compound CCC was used for comparison purposes.

Not only was growth height reduced—the leaves also took on a more intense color. The increased chlorophyll content is indicative of a higher rate of photosynthesis, making for bigger yields.

Comparative agent:

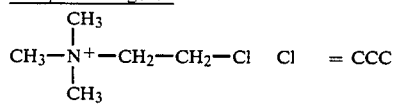

$$CH_3-\overset{CH_3}{\underset{CH_3}{N^+}}-CH_2-CH_2-Cl \quad Cl^- = CCC$$

TABLE 2

Soybeans
Postemergence treatment

| Ex. no. | mg of active ingredient per vessel | Growth height % |
| --- | --- | --- |
| untreated | — | 100 |
| CCC | 1.5 | 96.5 |
|  | 6.0 | 88.8 |
| 19 | 1.5 | 50.0 |
|  | 6.0 | 39.3 |
| 13 | 1.5 | 61.8 |
|  | 6.0 | 45.9 |
| 34 | 1.5 | 67.7 |
|  | 6.0 | 51.8 |
| 41 | 1.5 | 65.7 |
|  | 6.0 | 51.8 |
| 28 | 1.5 | 58.4 |
|  | 6.0 | 52.0 |
| 43 | 1.5 | 48.7 |
|  | 6.0 | 42.2 |
| 35 | 1.5 | 60.1 |
|  | 6.0 | 55.1 |

TABLE 3

Sunflowers
Postemergence treatment

| Ex. no. | mg of active ingredient per vessel | Growth height % |
| --- | --- | --- |
| untreated | — | 100 |
| CCC | 1.5 | 89.5 |
|  | 6.0 | 81.7 |
| 19 | 1.5 | 70.3 |
|  | 6.0 | 58.6 |
| 17 | 1.5 | 66.2 |
|  | 6.0 | 61.3 |
| 13 | 1.5 | 69.0 |
|  | 6.0 | 61.3 |
| 34 | 1.5 | 70.0 |
|  | 6.0 | 64.2 |
| 46 | 1.5 | 75.1 |
|  | 6.0 | 61.4 |
| 43 | 1.5 | 75.1 |
|  | 6.0 | 61.4 |

TABLE 4

Sunflowers
Postemergence treatment

| Ex. no. | mg of active ingredient per vessel | Growth height % |
| --- | --- | --- |
| untreated | — | 100 |
| CCC | 1.5 | 93.8 |
|  | 6 | 85.9 |
| 8 | 1.5 | 89.3 |
|  | 6 | 71.4 |
| 21 | 1.5 | 62.3 |
|  | 6 | 56.8 |
| 24 | 1.5 | 80.1 |
|  | 6 | 70.3 |
| 47 | 1.5 | 63.4 |
|  | 6 | 56.0 |
| 26 | 1.5 | 70.9 |
|  | 6 | 57.8 |

TABLE 5

Soybeans
Postemergence treatment

| Ex. no. | mg of active ingredient per vessel | Growth height % |
| --- | --- | --- |
| untreated | — | 100 |
| CCC | 0.5 | 97.1 |
|  | 1.5 | 97.1 |
| 21 | 0.5 | 80.2 |
|  | 1.5 | 73.8 |
| 24 | 0.5 | 78.1 |
|  | 1.5 | 69.6 |

We claim:

1. A method of regulating the upward growth of vegetable plants which comprises: applying to said plants a composition comprising an aqueous or solid carrier that is compatible with the growth regulating activity of the active agent and an effective amount of a phenylpropyl ammonium salt of the formula

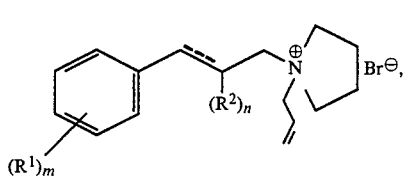

Ib where $R^1$ denotes alkyl of 1 to 6 carbon atoms, cyclopentyl, cyclohexyl, alkoxy of 1 to 6 carbon atoms, acetyl, propionyl or halogen, $R^2$ denotes alkyl of 1 to 6 carbon atoms, alkenyl of up to 6 carbon atoms or alkoxy of 1 to 6 carbon atoms, m denotes one of the integers 0, 1, 2 and 3, and n denotes one of the integers 1 and 2 and the dashed bond may be hydrogenated when n is 1, and is hydrogenated when n is 2.

2. A method as defined in claim 1, wherein the phenylpropyl ammonium salt is selected from the group consisting of N-allyl-N-[3-(2-fluorophenyl)-2methylpropyl]-pyrrolidinium bromide, N-ally-N-[3-(2,4-dichlorophenyl)-2-methylpropyl]-pyrrolidinium bromide, N-allyl-N-[3-(2,4-dichlorophenyl)-2-isopropylpropyl]-pyrrolidinium bromide, N-allyl-N-[3-(2,4-dichlorophenyl)-2-propylpropyl]-pyrrolidinium bromide, N-allyl-N-[2-methyl-3-(o-methylphenyl)-propyl]-pyrrolidinium bromide and N-allyl-N-[3-(4-chlorophenyl)-2-methylpropyl]-pyrrolidinium bromide.

3. A method as defined in claim 1, wherein the phenylpropyl ammonium salt is N-allyl-L-[2-methyl-3-(o-methyl-phenyl)-propyl]-propylpyrrolidinium bromide.

* * * * *

UNITED STATES PATENT AND TRADEMARK OFFICE
CERTIFICATE OF CORRECTION

PATENT NO. : 4,602,930

DATED : July 29, 1986

INVENTOR(S) : Buschmann et al.

It is certified that error appears in the above-identified patent and that said Letters Patent is hereby corrected as shown below:

Column 12, line 7 [L] should be: N

Column 11, line 7 [ally] should be: allyl

Signed and Sealed this
Second Day of December, 1986

Attest:

DONALD J. QUIGG

Attesting Officer

Commissioner of Patents and Trademarks